(12) United States Patent
Kriksunov et al.

(10) Patent No.: US 9,265,690 B2
(45) Date of Patent: Feb. 23, 2016

(54) ELECTRICAL STIMULATION DEVICE WITH ADDITIONAL SENSORY MODALITIES

(75) Inventors: Leo B. Kriksunov, Glenside, PA (US); Naomi Furgiuele, Doylestown, PA (US); Joshua Ghaim, Princeton, NJ (US); Aliya Omer, New York City, NY (US); Ronni Robinson, Ambler, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 1194 days.

(21) Appl. No.: 12/717,979

(22) Filed: Mar. 5, 2010

(65) Prior Publication Data

US 2010/0228304 A1 Sep. 9, 2010

Related U.S. Application Data

(60) Provisional application No. 61/158,157, filed on Mar. 6, 2009.

(51) Int. Cl.

| | | |
|---|---|---|
| *A61N 1/02* | (2006.01) | |
| *A61H 23/02* | (2006.01) | |
| *A61F 7/00* | (2006.01) | |
| *A61H 39/00* | (2006.01) | |
| *A61N 1/36* | (2006.01) | |
| *A61F 7/03* | (2006.01) | |
| *A61N 1/04* | (2006.01) | |
| *A61N 1/30* | (2006.01) | |
| *A61N 5/06* | (2006.01) | |

(52) U.S. Cl.
CPC .......... *A61H 23/0218* (2013.01); *A61F 7/007* (2013.01); *A61H 23/0263* (2013.01); *A61H 39/002* (2013.01); *A61N 1/36021* (2013.01); *A61F 7/034* (2013.01); *A61F 2007/0075* (2013.01); *A61N 1/0496* (2013.01); *A61N 1/303* (2013.01); *A61N 5/062* (2013.01); *A61N 2005/0651* (2013.01); *A61N 2005/0659* (2013.01); *A61N 2005/0661* (2013.01); *A61N 2005/0662* (2013.01)

(58) Field of Classification Search
CPC .......................... A61N 1/36021; A61N 1/205
USPC .................................... 607/3, 46, 66
See application file for complete search history.

(56) References Cited

U.S. PATENT DOCUMENTS

| 4,121,594 A | 10/1978 | Miller et al. |
| 4,583,547 A | 4/1986 | Granek et al. |
| 4,919,148 A | 4/1990 | Muccio |

(Continued)

FOREIGN PATENT DOCUMENTS

| EP | 1078649 B1 | 3/2008 |
| WO | WO 2006/038235 A2 | 4/2006 |
| WO | WO 2008/004159 A2 | 1/2008 |

OTHER PUBLICATIONS

International Search Report dated Jun. 2, 2010 for PCT/US2010/026322.

*Primary Examiner* — Carl H Layno
*Assistant Examiner* — Jennifer Ghand
(74) *Attorney, Agent, or Firm* — Victor Tsu (57) ABSTRACT

A therapeutic apparatus includes an electrical stimulation delivery device, and at least one secondary modality delivery device, wherein the secondary modality delivery device is in an active state during at least a portion of a refractory period of the electrical stimulation delivery device.

28 Claims, 3 Drawing Sheets

(56) References Cited

U.S. PATENT DOCUMENTS

| | | |
|---|---|---|
| 4,989,605 A | 2/1991 | Rossem |
| 5,354,321 A | 10/1994 | Berger |
| 5,423,874 A | 6/1995 | D'Alerta |
| 5,897,522 A | 4/1999 | Nitzan |
| 6,132,392 A | 10/2000 | Stone |
| 6,175,763 B1 | 1/2001 | Sorenson et al. |
| 6,275,372 B1 | 8/2001 | Vassallo et al. |
| 6,552,895 B1 | 4/2003 | Vassallo et al. |
| 7,483,738 B2 | 1/2009 | Tamarkin et al. |
| 2002/0077688 A1 | 6/2002 | Kirkland |
| 2003/0059673 A1 | 3/2003 | Langan et al. |
| 2004/0138712 A1 | 7/2004 | Tamarkin et al. |
| 2005/0043655 A1 | 2/2005 | Scheneck |
| 2006/0190057 A1 | 8/2006 | Reese |
| 2008/0021519 A1 | 1/2008 | De Geest et al. |
| 2009/0112283 A1 | 4/2009 | Kriksunov et al. |

ELECTRICAL STIMULATION DEVICE WITH ADDITIONAL SENSORY MODALITIES

CROSS REFERENCE TO RELATED APPLICATIONS

This application claims priority to U.S. provisional application Ser. No. 61/158,157, filed Mar. 6, 2009, the entire contents of which are incorporated by reference herein.

BACKGROUND OF THE INVENTION

1. Field of the Invention

The present invention relates to a device and method for reducing pain and assisting a patient with pain management. More particularly, the present invention relates to a device and method designed to assist in reducing pain through the use of electrical impulses.

2. Related Background Art

Transcutaneous electrical nerve stimulation (TENS) is a form of electrical therapy that applies controlled bursts of electrical impulses on the skin to the nervous system in order to reduce pain. TENS therapy is based on a non-invasive, non-narcotic concept of pain management. It is non-addictive, not subject to abuse and does not interact with oral or topical drugs. TENS has been proven to be an effective modality in the treatment of a variety of organic pain problems including: chronic neck and back pain, bursitis, arthritic disease, etc. A mild tingling sensation and possibly muscle twitch is felt by the patient using a TENS device. A patient may use a TENS device numerous times throughout the day in various locations.

TENS devices are known for delivering electromagnetic stimulation as disclosed in U.S. Pat. No. 4,121,594 titled, "Transcutaneous Electrical Nerve Stimulator," (Miller et al.) and U.S. Pat. No. 5,423,874 titled, "Patch for Applying Pain Reducing Energy to the Body" (D'Alerta et al.). TENS devices deliver DC current in a range greater than 1 milliampere, typically at about 5 to 20 milliamperes.

Microcurrent electrical stimulation is a form of electrical therapy that applies a current of less than one milliampere, typically in the range of about 20-500 microamperes, or about less than about 1 milliampere. U.S. Pat. No. 5,354,321 discloses devices that are used in the application of therapeutic microcurrent. One characteristic inherent in microcurrent devices is that the current that is supplied is below the sensory threshold of and therefore not felt by the user. Even though the current is being applied, the user generally does not feel that the device is working to treat pain.

U.S. Pat. No. 7,483,738 to Tamarkin et al. discloses a combination of a stimulating device and an exothermic heating component and its method of use. Examples of the eothermicheating component include mixtures of oxidizable material and carbon and metallic compositions.

U.S. application no. 20080021519 discloses an electric communication unit that comprises a support element that comprises a series of body contacts and a pulse generator connected to the series of body contacts. The pulse generator generates a series of pulses upon receipt of a first signal and transmits them to the series of body contacts. The pulse generator further comprises a processing unit with a memory. The processing unit stores a second signal that comprises data indicative at which time the first signal should be generated.

U.S. Pat. No. 6,175,763 to Alza discloses an electrotransport drug delivery system which can signal, to a patient wearing the system, an occurrence of an event or condition associated with operation of the system, that comprises an electrotransport drug delivery system including a pair of electrodes, at least one of which has a reservoir attached thereto, through which an electrotransport drug delivering current is applied to the patient; a sensor connected to the system for sensing an event or condition associated with the operation of the system; a tactile signal generator connected to the system, responsive to the sensor, for generating and transmitting an electric tactile signaling current through the pair of electrodes to the patient, the signaling current having a magnitude and waveform shape which is capable of being felt by the patient and which delivers little to no net drug to the patient.

U.S. application no. 20090112283 to Kriksunov et al. discloses an apparatus that includes a microcurrent delivery device and at least one independent sensory cue that is activated upon application of the device.

There remains a need for a device and method that provides an indication to the user that the device is providing effective treatment of pain throughout its entire intended period of use.

It is an object of the present invention to provide a device and method that provides an indication to the user that the device is providing effective treatment of pain throughout its intended period of use. These and other objects and advantages of the invention will become apparent in light of the description below.

SUMMARY OF THE INVENTION

The present invention is directed to an electrical stimulation device that comprises an electrical stimulation delivery device means and at least one secondary modality delivery means, wherein the secondary modality delivery means is in an active state during at least a portion of a refractory period of the electrical stimulation delivery means.

The present invention also includes a method of reducing pain and/or the symptoms of other inflammatory conditions in a subject experiencing pain and/or other inflammatory conditions, comprising the step of treating the subject with an electrical stimulation device that comprises an electrical stimulation delivery means and at least one secondary modality delivery means, wherein the secondary modality delivery means is in an active state during at least a portion of a refractory period of the electrical stimulation delivery means.

In an alternative embodiment, the present invention is a method of preparing muscles for exertion and or stretching muscles comprising the step of treating the subject with an electrical stimulation device that comprises an electrical stimulation delivery means and at least one secondary modality delivery means, wherein the secondary modality delivery means is in an active state during at least a portion of a refractory period of the electrical stimulation delivery means.

DETAILED DESCRIPTION OF THE INVENTION

All publications cited herein are hereby incorporated by reference. Unless defined otherwise, all technical and scientific terms used herein have the same meaning as commonly understood to one of ordinary skill in the art to which the invention pertains.

As used herein "refractory period" refers to the time period in which the device is not delivering electric stimulation. Constant electrical stimulation to the body may lead to side-effects, sensitization and diminished therapeutic effects. Additional side-effects, may include desensitization to the electrical stimulation treatment, numbness and overall discomfort. As such, electrical stimulation treatment may be administered on a cyclical basis. That is, the electrical stimulation device may be programmed to provide cyclical treatment to a subject. In this situation, the subject receives relief during the treatment period, however, during the refractory period, the subject may be treated with a second modality treatment. Electrical stimulation devices are typically turned on for a certain period of time, and switched off after the treatment. Instead of being turned off, electrical stimulation can be put in a low power treatment state (e.g. sub-sensory treatment level) or dormant state.

The secondary modality delivery means may provide (i) treatment during at least a portion of the refractory periods, and/or (ii) sensory fill-in during at least a portion of the refractory periods, thus continually providing pain relief even when the electrical stimulation device is not providing therapeutic treatment/relief.

It is desirable to have a single device which need not be removed during refractory periods when the electrical stimulation is not delivered. The invention disclosed herein is directed to a combinatorial device which provides at least one independent sensory treatment modality, e.g., secondary modality, during the refractory periods, i.e., when electrical stimulation is not applied to the subject. The refractory period may be at the beginning, in the middle or at the end of the application of electrical stimulation, and may consist of one or more periods of time during the treatment phase. Secondary modalities, such as vibration, heat, light therapy, and chemical sensates are in an active state when electrical stimulation is de-activated. A combination medical device adapted to deliver at least one treatment or sensory fill-in modality in addition to electrical stimulation is disclosed. In one embodiment, the secondary modality treatment is delivered at a level (in an effective amount) at which a therapeutic pain relief is experienced by the subject. In another embodiment, the secondary modality treatment is delivered as a sensory cue to let the subject know that the device is functioning within a refractory period. All modalities are delivered from an integrated medical device. The integrated device may be pre-programmed, electronically or mechanically activated to deliver these modalities during the refractory periods. The device disclosed herein is used to treat pain, and other inflammatory conditions including, but not limited to generalized localized pain, chronic pain, joint pain, muscle pain, back pain, rheumatic pain, arthritis, wound treatment, osteoarthritis and combinations thereof. In one embodiment the secondary modality is delivered as a sensorial or sensory cue. In another embodiment, the sensory cue is delivered in a continuous and uninterrupted manner. In another embodiment, the sensory cue is delivered in an interrupted or periodic manner, particularly during periods when electrical stimulation is interrupted or between electrical stimulation treatments. Examples of suitable independent sensory cues include, but are not limited to, vibration, heating, cooling, ultrasound, auditory cues or alternatively, via chemical cues such as fragrances, heating sensates, heating analgesics, and cooling sensates. In one embodiment, a sensory cue is sensed by the subject even when the device is worn under the subject's clothing and is not directly visible to the subject. In another embodiment, a sensory cue is delivered to indicate to the subject that the electrical stimulation device is not working.

The secondary modality treatments may be delivered in the form of energy including, but not limited to, for example, vibration, heating, cooling, detectable electrical pulses, ultrasound, or alternatively, via chemical cues, heating sensates, heating analgesics and cooling sensates. In addition, a temperature control feature can be integrated into the device through the use of phase change materials or other means of regulating temperature through exothermic reduction-oxidation reactions or by other means of electrical heating.

The electrodes can be fabric-based, hydrogel-based, metal or carbon based, direct skin contact electrodes, etc. The electrodes can further be of the same size and shape or of different size and shape.

The electric parameters of electrostimulation can provide sensory treatment and subsensory treatment; ac, dc, and pulse treatment, symmetric and non-symmetric pulses of different duty cycle, amplitude, frequency, and shape, modulated, and non-modulated, and with different ramp-up. The treatment can correspond to treatment parameters known in the art as TENS, microcurrent, faradic current, galvanic current, high voltage pulsed current, Russian current, interferential current, diadynamic current, Functional Electrical Stimulation, Neuromuscular Electrical Stimulation.

Figure 1:
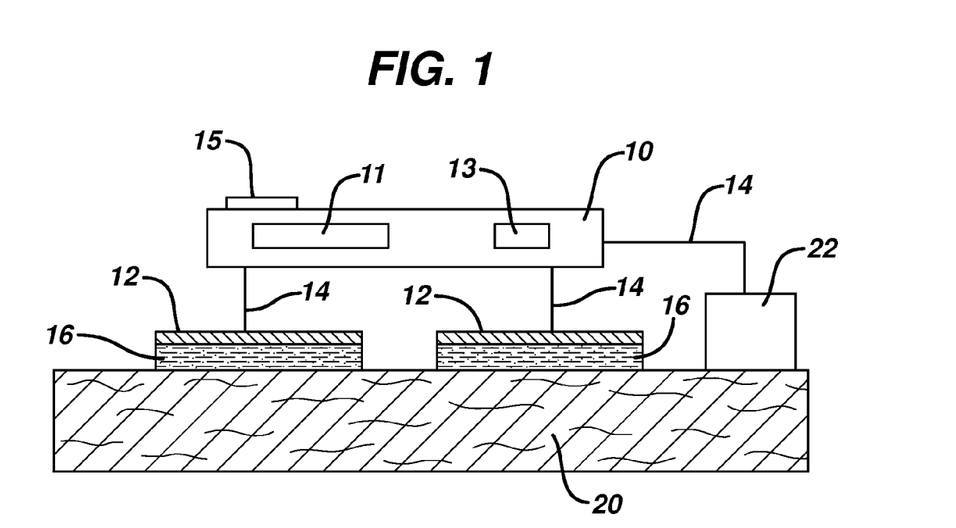
FIG. 1 depicts a schematic cross-sectional view of a wired embodiment of the invention, with a housing containing electronic components and power supply connected to the electrostimulation electrodes and secondary stimulation modality via wired connections.
Figure 2:
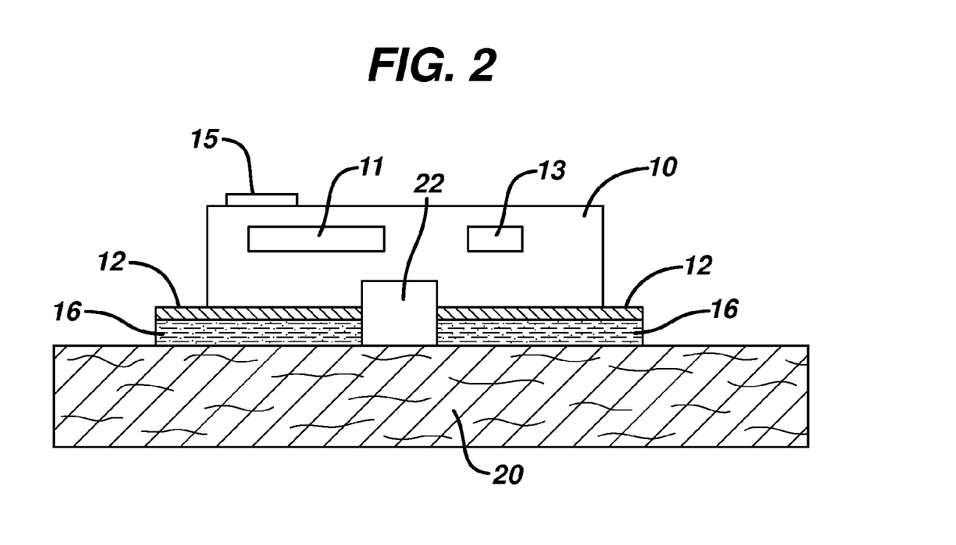
FIG. 2 depicts a schematic cross-sectional view of a wireless embodiment of the invention, with a housing containing electronic components and power supply integrated with the electrostimulation electrodes and secondary stimulation modality in a unified patch.

FIGS. 1 and 2 illustrate schematic cross-sectional views of wired (FIG. 1) and integrated wireless (FIG. 2) embodiments of electrostimulation devices with secondary modality of the present invention, with devices positioned on the body of a user in direct contact with the skin. A TENS device, in one embodiment, includes a housing 10 containing electronic circuit 11 with current generator capable of generating high voltage pulses for therapeutic treatment through electrode pads 12, power supply means 13, and optional control means 15. Control means 15 are positioned on the outside of the housing for easy access of the user, and may include on/off switches, amplitude and/or frequency control switches and adjustment levers, light indicators, program selectors, and other controls for programming and customizing the treatment. Alternatively, control means 15 can be positioned as a remote control device, wirelessly communicating with the electronic circuit 11. Conductive lines 14 in the wired embodiment of FIG. 1 provide an electrical connection from the electronic circuit 11 to electrode pads 12. Electrode pads 12 can be provided with optional carrier 16, such as a hydrogel coating, that, when the therapy device is in use, are positioned between the exterior surface 20 of the body of the patient and electrode pads 12. Conductive lines 14 in the integrated or wireless embodiment shown in FIG. 2 are integrated within the housing 10 of the device and are not shown in FIG. 2.

Secondary modality or sensory cue means 22, as exemplified by, for example, heat, cold, vibration, chemical sensate, or light, are positioned in contact with the patient's body. In one embodiment, secondary modality means are positioned remotely from electrode pads 12 and housing 10 as shown in FIG. 1. Conductive lines 14 in the wired embodiment of FIG. 1 provide an electrical connection from the electronic circuit 11 to secondary modality means 22. In another embodiment, secondary modality means 22 is positioned proximally to electrode pads 12 and the housing 10 and as exemplified in FIG. 2 is integrated within the housing 10.

In yet another embodiment, secondary modality means 22 are temporarily affixed to the patient's body through a hydrogel or adhesive media or through a non-adhesive thermally conductive media such as gels, polymers, metals, or composites. In another embodiment (not shown), secondary modality means 22 are positioned behind the electrode pads 12 and supply sensory cues such as heat or vibratory directly through electrode pads 12.

Secondary modality means or sensory cue means 22 shown in FIGS. 1 and 2 can be vibratory, electric, thermal, and sensate sensory cue means, or combination thereof.

Figure 3:
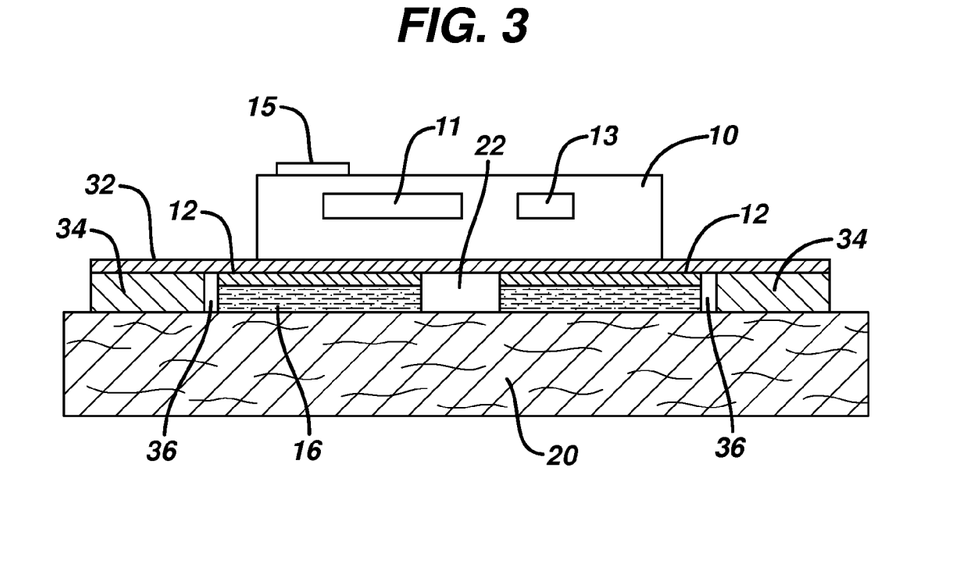
FIG. 3 depicts a schematic cross-sectional view of a wireless embodiment of the invention, with a housing containing electronic components and power supply being integrated with the electrostimulation electrodes and two secondary stimulation modalities.

Referring to FIG. 3, an embodiment of an integrated or wireless electrostimulation device with secondary modality is shown. Electrode pads 12 having optional hydrogel coating 16 are positioned on the exterior surface 20 of the body of the patient and are supported on a flexible support backing 32 in connection with the device housing 10. Chemical sensates modality or sensory cue means 34 are positioned in contact with the exterior surface 20 of the patient's body and are supported on a flexible support backing 32 in connection with the device housing 10. Chemical sensates feedback or sensory cue means 34 incorporate hydrogel or a coating, which can optionally be adhesive containing sensates. In one embodiment, there is a spacer or a gap 36 between chemical sensates or sensory cue means 34 and electrode pads 12. In another embodiment (not shown), there is no gap or spacer between chemical sensates modality or sensory cue means 34 and electrode pads 12. In yet another embodiment (not shown), chemical sensates sensory cue means are incorporated into the hydrogel or other conductive coating on electrode pads. The embodiment shown in FIG. 3 can optionally also incorporate secondary modality means or sensory cue means 22 such as thermal or vibratory modality in addition to the chemical sensates modality 34.

The present invention relates to a device for the delivery of electricity, (e.g., to induce a desirable biological response) into a barrier membrane or skin and is coupled with an independent secondary modality treatment means, or consumer signal, or sensory cue, including vibratory, thermal, sensates, and similar, which are delivered during refractory periods. In one embodiment, the device of the present invention is a self-contained device that provides at least one independent sensory cue, the device having at least one pair of conductive electrodes 12 wherein each electrode 12 is contained in a separated compartment or carrier and is affixed to the skin with electric insulation between the pair of electrodes 12 so that all of the electric current generated by the device travels through the skin and underlying tissue to complete the electric circuit. A power source can be connected to the pair of electrodes 12. Alternatively, the two conductive electrodes 12 can be formed using a pair of two dissimilar conductive electrodes 12 in electric communication as a power source.

Secondary Modality

The secondary modality, which can be any physical or chemical signal or mode of action, provides an impact on the body and results in therapeutic relief.

In one embodiment, the secondary modality is heat delivered via electronic means.

In another embodiment, the secondary modality is heat delivered via exothermic chemical means.

In yet another embodiment, the secondary modality is vibration.

In still another embodiment, the secondary modality is light therapy.

In still yet another embodiment, the secondary modality is a chemical sensate.

The secondary modality is provided through an element that is in contact with the patient's body. The element may be a heating or cooling element, a vibratory element, or a LED light source.

Thermal Cue Means or Hot/Cold Modality

In one embodiment, a thermal sensory modality means is in direct or indirect contact with a subject's skin and provides a heating or cooling sensation. In another embodiment, every 3 minutes, every 5 minutes, or every 10 minutes, a short pulse of heating or cooling is provided as a sensory cue. In still another embodiment, the length of the pulse is 3 seconds, 10 seconds, or 1 minute. The heating or cooling is performed to vary the temperature on the skin by several degrees, for example, by about 3° C. to about 10° C. The temperature change is selected so as to provide a sensory cue, while simultaneously avoiding any overheating or overcooling of the skin.

The heating is performed using an electric heating element, such as an electric resistive heating element. In one embodiment, cooling is applied as a sensory cue utilizing Peltier devices. In another embodiment, warming is applied as a sensory cue utilizing Peltier devices.

The thermal cue is provided by an electrically powered heating element or a cooling element, or both. Electrically heated elements include resistively heated elements such as those consisting of conductive metallic traces on flexible supports. Other types of heaters are, for example, composite resistive heaters wherein the conductive area is formed by substantially uniform coating of conductive paste or conductive coating, such as silver-powder plus non-conductive binder or carbon-powder plus non-conductive binder paste or coating. The conductive elements of the above heaters can be encapsulated between two layers of generally non-conductive materials or they can be supported on top of one substantially non-conductive supporting layer. Other types of resistively heated elements, include conductive ceramic elements, conductive tapes, insulated wire-based elements, and conductive coatings such as indium-tin oxide coating, and other types of heating elements. Thermo-electric elements, also known as Peltier elements, can also be utilized to provide a heating or cooling sensory cue using electric power. Yet another type of element providing a thermal cue is based on a micro-fan element, which is blowing ambient air on the skin. This element is utilizing cooling energy of ambient air to supply a cooling sensation and thus provide a thermal cue.

The circuit to power the electrically heated or cooled element includes a power supply, a current and/or voltage controller, as well as a timing circuit. Timing circuits, power supplies, and current and/or voltage controllers are widely available. Electric energy from the power supply is supplied to the electric heating or cooling element at pre-programmed times, controlled by the timing circuit. In one embodiment, the thermal cue is provided continuously, or each 15 seconds, or each 30 seconds, or each 2 minutes, or each 5 minutes, or each 10 minutes, or at similar time intervals. In another embodiment, the heating or cooling is performed for 5 seconds, 10 seconds, 30 seconds, or 2 minutes or for similar time intervals. In still another embodiment, the heating or cooling is provided to change the temperature of the element by 5° C., 10° C., 15° C., or by 20° C., or by similar temperature increments, either by heating or cooling. In still yet another embodiment, the heating or cooling is provided during refractory periods of electrical stimulation, i.e., when the electrical stimulation device is not providing treatment or between treatments. The power supply used to power the electrically heated or cooled element can be the same power supply used to power the electrical stimulation, or it can be a separate power supply specifically designated to power the electrically heated or cooled element. In yet another embodiment, the thermal cue is provided by a heating pack, such as a pack containing an iron-carbon-water exothermic powder mixture, which is heated upon contact with air. In this embodiment the heating cue is provided constantly throughout the treatment or while the heating pack is active.

FIGS. 1-3 depict an embodiment in which the heater is an electrically powered resistive heater element directly in contact with the body. The heating element can be made of any conductive material with appropriate resistance, including metals and metal alloys, conductive polymers, composite materials, conductive fabrics, conductive filaments encapsulated in non-conductive supports, and the like.

Figure 4:
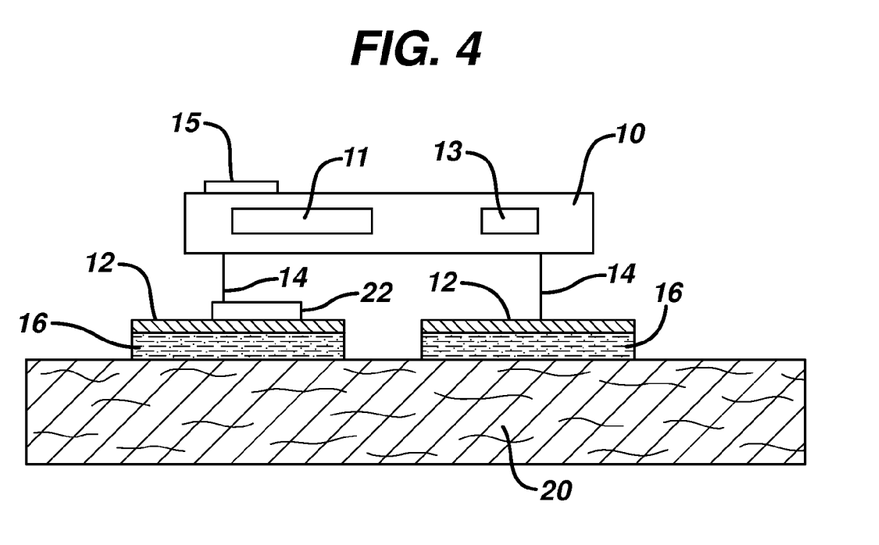
FIG. 4 depicts a schematic cross-sectional view of a wired embodiment of the invention, with a housing containing electronic components and power supply connected to the electrostimulation electrodes and secondary stimulation modality via wired connections, with the secondary stimulation modality mounted on one of the electrostimulation electrodes.

In another embodiment schematically illustrated in FIG. 4, the secondary modality means 22 is combined with or mounted on, at least one of the electrical stimulation electrodes 12. The secondary modality means 22 may be a thermal element, such as a heating or cooling element. The thermal effects from the secondary modality means 22 are transferred to the exterior surface 20 of the patient's body. In another embodiment (not shown), the electrical stimulation electrode is made of a material having appropriate resistivity and thickness, for example, carbon or silver composite. At least between electrical stimulation treatments (and optionally also during electrical stimulation treatment), a current is passed laterally (i.e., in the plane of the electrode) from one edge of the electrical stimulation electrodes to another using appropriate electric interconnects. The electrode then acts as a resistive heater. The heat is then delivered to the body due to the increased temperature of the electrode. The electric current used to heat up the electrical stimulation electrode can be dc current or ac current or a combination of both.

Vibratory Modality or Vibratory Cue Means

Referring to FIGS. 1-4, the secondary modality 22 can be a vibratory modality, with a vibratory element. The vibratory element can be any vibrating mechanism known in the art, including an electric motor with offset weight located on the rotor, a stop-and-go electric motor, linear motors operated in a back and forth fashion, a piezo-electric vibrator, an electric solenoid vibrator, or other vibrator type known in the art. In one embodiment, the rotation of the eccentric mass about the axis of the motor creates the vibrator effect, the speed of rotation establishing the frequency of vibration. The motor and mass preferably are contained in an enclosure to shield the rotating members from disturbance. The degree of force can be tuned by adjusting or selecting the following parameters, speed (frequency of oscillation) amount of eccentric mass, degree of offset of mass from centerline, and amount of moving mass. An example of a vibratory system which employs simple off the shelf components could include commercially available vibratory elements such as low voltage dc motors with eccentric weights which are designed for commercial products such as mobile phones, electric tooth brushes, toy vehicles, and massagers. Other electro-magnetic vibratory mechanisms known in the art utilize an electro-magnetic coil that is energized with an alternating current to generate an alternating magnetic field, which in turn results in oscillations of a metallic component.

Figure 5:
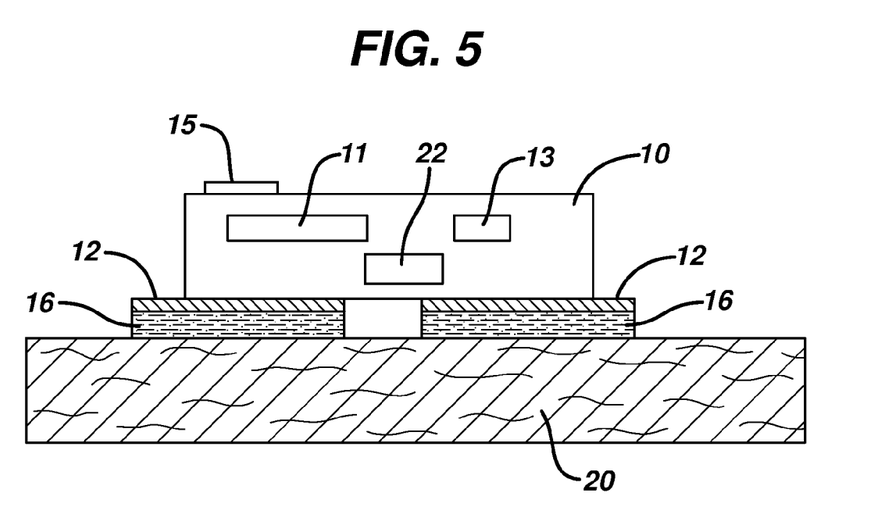
FIG. 5 depicts a schematic cross-sectional view of a wireless embodiment of the invention, with a housing containing electronic components and power supply being integrated with the electrostimulation electrodes and the secondary stimulation modality, with the secondary stimulation modality mounted inside of the housing.

Referring to FIG. 5, the secondary modality 22 is a vibratory modality, incorporated into housing 10.

In one embodiment, vibration is combined in an electrical stimulation device and supplied as the independent sensory cue to the subject. Vibration can be added as a periodic pulse at a specified time interval. In one embodiment, the vibration is administered at time intervals of every 60 minutes, e.g., every 30 minutes, e.g., every 10 minutes, e.g., every 5 minutes, e.g., every 1 minute, e.g., every 30 seconds or time periods that correlate with treatment end and start points. Vibratory energy can be supplied in a device using various mechanisms including, but not limited to, delivery via electro-magnetic vibratory mechanism, piezo-ceramics or piezo-polymer based vibratory mechanism, or an electric micro-motor, including micro-motor having a rotor with an offset center of mass, or other vibratory mechanism known in the art. The intensity and frequency of vibration is selected so as to provide a detectable sensation to the subject of the device.

In one embodiment, a vibration with the frequency of from about 1 Hz to about 50 KHz is utilized and with amplitude of from 1 micron to 5 mm peak-to-peak or a singular event, rather than multitude of vibrations. The vibratory energy is sensed by the subject's skin and is transferred to the skin in its entirety directly to the skin or indirectly through the device.

In one embodiment, a vibratory cue means is in direct contact with the patient's body and thus directly transfers the vibratory energy to the patient's body. In another embodiment, the vibratory sensation is transmitted to the patient though an air gap. In yet another embodiment, the vibratory sensation is transmitted to the device or components thereof.

Light Modality or Light Therapy Means

Alternatively, the secondary modality 22 is a light delivery element, such as a Light Emitting Diode (LED) providing visible light, IR radiation, UV light, or combination thereof.

In one embodiment, the device contains one or more light emitting diodes that can function to provide light therapy for treatment of various conditions or effect delivery of active agents. Light emitting diodes (LEDs) of certain spectrum may be incorporated into the device to emit light to the barrier membrane. The light emitting diode may also provide a signal to the subject indicating that the device is operating properly.

The spectrum of the LED's according to the current invention may range from about 300 nm to about 1500 nm, such as from about 350 nm to about 1000 nm. In one embodiment, the range of the LED includes violet-blue, green, red, and infra-red ranges, e.g., from about 400 nm to about 450 nm such as from about 407 nm to about 420 nm; from about 510 nm to about 550 nm; from about 600 nm to about 700 nm; and from about 1300 nm to about 1500 nm. In one embodiment, the device contains two LEDs, one that emits light having a wavelength of from about 400 nm to about 500 nm and one which emits light having a wavelength from about 700 nm to about 1000 nm. Photosensitizer agents, such as 5-aminolaevulinic acid (ALA), hypericin, St. John's wort powder or extract, or other synthetic or natural photosensitizer agents, may be incorporated into the carrier as active agents to be delivered and irradiated by the device with LED's of the present invention.

In one embodiment the LED functions in the infrared range, and subsequently provides heat, which functions as the sensory cue described herein.

Chemical Sensate Secondary Modality

In one embodiment, the conductive gel is formulated to contain a sensate, e.g., any of the U.S. Monograph topical monograph counterirritants (e.g., Camphor >3% to 11%; Menthol 1.25-16%; Histamine; dihydrochloride 0.025-0.10%; Methyl nicotinate 0.25-1%; Capsaicin 0.025-0.25%; Capsicum containing 0.025-0.25% capsaicin; Capsicum oleoresin containing 0.025-0.25% capsaicin; Allyl isothiocyanate 0.5-5%; Methyl salicylate 10-60%; Turpentine oil 6-50%), or any known topical cooling, warming, or tingling agent, for example [(−)-isopulegol, (2S)-3-(1-methoxy)propane-1,2-diol, "Frescolat MGA"/menthone glycerin acetal, "Frescolat ML"/menthyl lactate, "WS-14"/N-t-butyl-p-menthane-3-carboxamide, "WS-23"/2-Isopropyl-N,2,3-trimethylbutyramide, WS-12/N-(4-methoxyphenyl)-p-menthane-3-carboxamide, "WS-3"/N-Ethyl-p-menthane-3-carboxamide, and "WS-5"/Ethyl 3-(p-menthane-3-carboxamido)acetate].

In another embodiment, the sensate is contained in any part of the device that has a direct interface with the patient's skin.

In one embodiment, a chemical agent is applied to the surface of the device that is applied to the skin. This chemical agent can be available as a fragrance, cooling agent, or heating agent to indicate to the consumer that the device is associated with pain relief. In another embodiment, the chemical agent is supplied as a topical analgesic in order to provide not only the sensory cue, but also immediate pain relief to accommodate the delay in relief that may be provided by the electrical stimulation therapy. The chemical agent may be added to the hydrogel, which is in turn added to the pad of the device, which is then applied to the skin. Optionally, there may be a separate pad or portion of the device which meters out the chemical agent at specified time intervals. In still another embodiment, the subject may be able to physically rub a portion of the device containing the chemical sensory cue in order to deliver the chemical through a pad to the surface of the skin. In one embodiment, the chemical agent is separated from the electrodes by means of a barrier. In this embodiment, the barrier prevents the electrical stimulation from affecting the rate or penetration of the chemical agent into the skin. In this embodiment, the rate and penetration of the chemical agent though the skin and muscle tissue is the same during the active and refractory periods of electrical stimulation.

Topical analgesics are a well known class of compounds and include, but are not limited to, counter irritants such as, for example, menthol, methyl salicylate, camphor, topical capsaicin, capsicum oleoresin, choline salicylate, ethyl salicylate, glycol salicylate, salicylic acid, and turpentine oil; NSAIDs such as, but not limited to, diclofenac, felbinac, ibuprofen, ketoprofen, piroxicam, naproxen, and flurbiprofen; local anesthetics such as, but not limited to lignocaine, lidocaine and benzocaine; and other active ingredients such as, but not limited to, benzydamine, mucopolysaccharide polysulphate, and salicylamide.

Examples of anti-inflammatory agents, include, but are not limited to, suitable steroidal anti-inflammatory agents such as corticosteroids including, for example, hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, mepredisone, paramethasone, prednisolone, prednisone, beclomethasone dipropionate, betamethasone dipropionate, triamcinolone, and salts of prodrugs thereof. The preferred steroidal anti-inflammatory for use in the present invention is hydrocortisone. A second class of anti-inflammatory agents, which is useful in the compositions of the present invention includes nonsteroidal anti-inflammatory agents.

In one embodiment, a first chemical agent is added as a sensory cue and an additional second active chemical agent is added at a level at which a therapeutic amount of the agent is present to relieve pain.

Cooling agents may be sensates or chemicals, which provide a sensory cooling effect on the skin, immediately or delayed, inhibit heat receptors or stimulate cooling receptors and include but are not limited to non volatile cooling agents, cooling sugars, cooling adjuvants, urea, polyvinyl alcohols, eucalyptus, polyacrylic acid, menthyl succinate, monomenthyl succinate, carboximides, acyclic carboximides, mannitol, p-menthane carboxamide, and peppermint oil.

"Cooling sugars," as described herein, shall include all sugar alcohols that have negative heats of solution (enthalpy, $\Delta H < 0$ J/mol) and are known to impart some cooling sensation when placed upon the tongue of a subject.

"Cooling adjutants," as described herein, shall refer to all compounds that have a negative heats of solution (i.e., an enthalpy, $\Delta H$ of less that $<0$ J/mol). Examples of suitable cooling adjutants include, but are not limited to cooling sugars.

Timing Means

In one embodiment an internal clock exists in the device to control the delivery of the secondary modality. In the case of vibration, ultrasound, LED generated heat or electrically generated heating or cooling the clock signals to the cue to turn itself on or off and for a specified period of time. In another embodiment, the internal clock functions to time the physical release of a barrier, which in turn releases a chemical agent (warming, cooling, and fragrance). In still another embodiment, the internal clock functions to time the physical release of a membrane or portions of a membrane, which allows for oxygen to permeate and begin an exothermic reaction, which in turn, generates heat. The clock's drift is less than approximately 1 minute per week. The electrical stimulation portion may be delivered in a variety of time periods from about 1 minute to about 60 minutes and at various intervals in between, e.g., from about 1 minute to about 30 minutes, e.g., from about 1 minute to about 20 minutes.

Electrical Stimulation Subsystem

The electrical stimulation subsystem includes the following main components: power supply, electronic circuit, electrodes for interfacing with the skin, and control means. The control means may include a LCD screen and control buttons to activate the device and select treatment options. In one embodiment, the device is controlled via a remote control unit in RF communication with the electronic circuit.

Electrical Stimulation Secondary Modality

Electrical stimulation itself can be used as a secondary modality during the refractory period as a sensory cue or feedback to the patient that the primary electrical stimulation is in the refractory period. According to an embodiment, the sensory cue electrical stimulation is applied between the sensory threshold and the motor threshold so that the user can feel the sensation, but the sensation does not cause muscle contraction or only minor muscle contraction. Further, the stimulation is applied at a level, which does not cause an uncomfortable or painful feeling. The level of stimulation necessary to achieve these objectives varies from person to person. Literature data on the sensory threshold, motor threshold, and pain threshold are also variable. In addition, the sensory threshold, motor threshold, and the pain threshold are a function of the surface area of the stimulation. Additional variables that affect the thresholds are current density, region of the body, the length of the electric impulse and of the frequency of impulses. Higher current density will typically result in stronger sensation.

Electric pulses or bursts can be delivered through the same electrodes to provide the independent sensory cue. The main difference is related to providing electric pulses not as a treatment but at the lower level of sensation, typically characterized by lower amplitude and/or lower overall amount of pulses. Alternatively, intermittent, spaced in time bursts of pulses are delivered at the same or lower level of sensation. such bursts can be delivered, for example, every 1 min, every 5 min, or every 10 min, with 3 to 10 or up to 20-30 electric pulses identical or similar to TENS pulses or to the pulses delivered during the main treatment phase.

In one embodiment, the sensory cue impulses are applied at a 10 microsecond duration and at above about 50V, but below about 130V. In another embodiment, the sensory cue impulses are applied at a 10 microsecond duration and at above about 50V, but below about 250 V. In another embodiment, the sensory cue impulses are applied at about a 50 microsecond duration and at about 30V. In yet another embodiment, the user can adjust the voltage and/or pulse duration and/or frequency of pulses for sensory cue feedback for a desired sensation level.

The electric sensory cue impulses can be administered at time intervals of every 60 minutes, e.g. every 30 minutes, e.g. every 10 minutes, e.g. every 5 minutes, e.g. every 1 minute, e.g. every 30 seconds.

In one embodiment the electric sensory cue is applied using a pulse width of 1 micro-seconds to 10 milliseconds, e.g. from 10 micro-seconds to 1 millisecond.

In one embodiment the electric sensory cue is applied using a burst, which consists of a series of pulses that are separated by at least a discernible gap between each series of pulses.

In an embodiment, the same electrodes that are used to deliver primary electrical stimulation are also used to deliver the secondary electrical stimulation sensory cue. Electric circuits capable of delivering two levels of voltages and currents are known to these skilled in the art.

In one embodiment, the pulse is raised in less than 5 microseconds, or less than 1 micro-second; and falls in less than 5 micro-seconds, or less than 1 micro-second. In one embodiment, a high current (e.g. 5-20 mA) short duration pulses are supplied through the same electrodes as the micro-current therapy (e.g. 20-50 microamp) current. The high current impulses are selected to result in a detectable sensation similar to TENS, but with much shorter or intermittently applied pulses, e.g. three 100 microsecond pulses at 100 Hz every 60 seconds or every 5 minutes.

In one embodiment, the independent sensory cue is delivered through a separate electrical pulse, such as a current that is delivered at a voltage level at certain duration that can be sensed by the user. An electrical pulse can be delivered at a stimulus amplitude voltage that is above the sensory threshold, but below the pain tolerance limit.

The sensed electrical pulse cue is felt intermittently to let the user know that the device is working, especially when applied during the refractory period. In one embodiment the pulse is delivered at the start of the refractory period (when primary electrical stimulation treatment is stopped) and throughout the refractory period. In one embodiment, the pulse is delivered above the sensory threshold but below the motor threshold at which the muscles contract. The pulse of electric current can be delivered through the same or separate circuit through the same electrical stimulation electrode pads.

Power Source Means

In certain embodiments, the power source may be a single-use battery, such as either button cell shaped or cylindrical cell shaped or flat-pouch encapsulated battery based on any chemical composition known in the art, including manganese-zinc, metal hydride, lithium, lithium ion, and other known battery chemistries. The voltage of the battery can range from about 1 V to 3 V to about 12V. The battery capacity is selected to provide for sufficient time of operation of the electrical stimulation device and of the secondary modality means. Suitable power sources may include primary batteries and secondary (rechargeable) batteries, fuel cells, printed batteries, and plug-in power sources.

In one embodiment, the power source is a battery (e.g., a rechargeable or disposable battery). The battery may be, for example, a disposable battery of small size suitable for a wearable patch type adhesive device. Examples of suitable batteries include, but are not limited to, button or coin batteries such as silver oxide, lithium, and zinc air batteries (which are typically used in small electronic devices). A zinc air battery is preferred because of its small size and high energy density, as well as its environmental friendliness. Examples of zinc air batteries include, but are not limited to, Energizer® AC5 and AC10/230 (Eveready Battery Co. Inc., St. Louis, Mo.) or their equivalents. Another preferred battery for the device is a flexible thin layer open liquid state electrochemical cell battery, such as a battery described in U.S. Pat. No. 5,897,522 and published U.S. Patent Application No. 2003/0059673A1. In another embodiment, the power source is a rechargeable battery, such as a Ni—Cd, Ni-MH, or Li-Ion rechargeable battery well known in the art. In another embodiment, the power source is a rechargeable supercapacitor, such as described in U.S. Pat. Nos. 6,552,895 and 6,275,372.

The power source may be integrated into the device so that the device is portable and has no need for plugging into an external power source.

It should be understood, however, that other power source options may be used with the present invention. For example, the device may be configured such that the electrical stimulation delivery means portion has its own power source and/or the secondary modality delivery means portion of the device has its own power source.

Carrier

Optionally, the present invention may include a carrier. The carrier may be employed for example, to improve adhesion of the device to the skin and/or to facilitate the flow of current into the skin. In FIGS. 1-4, carriers 16 of the present invention can be a liquid (e.g., a solution, a suspension, or an emulsion which may be immobilized within an absorbent material such as gauze or a non-woven pad), a semi-solid (e.g., a gel, a cream, a lotion, microemulsion, or hydrogel), or a solid (e.g., a lyophilized composition containing active agents, which may be reconstituted by adding a liquid prior to use) that during use is capable of conducting electricity from a conducting electrode (e.g., the carrier contains one or more electrolytes, organic solvents, and water). In one embodiment, a chemical sensory cue is incorporated into the carrier.

The carrier (e.g., a liquid or semi-solid) may be added to the device by the subject prior to applying the device to the barrier membrane. For example, the carrier is added to a reservoir in the device such that upon addition into the reservoir, both the conductive electrodes (e.g., the anode and the cathode) are in ionic communication with the carrier (e.g., the conductive electrodes are within or in contact with the reservoir). The reservoir may be a chamber containing the electrodes or an absorbent material that can immobilize the carrier (such as gauze or a non-woven pad) that contains it or is in contact with the electrodes (e.g., the electrodes are contained within or affixed to the absorbent material).

The carrier may be manufactured and placed in storage as a stable nonconductive composition (e.g., an anhydrous composition with negligible conductive ions). Prior to or during use, as an activation step, water is mixed into the anhydrous composition to significantly increase its conductivity by enabling the passage of an electric current through the system. Examples of the carrier include, but are not limited to, skin creams, lotions, shampoos, moisturizers, skin toners, and cleansers. Other examples of carriers include biological fluids or excretion such as sweat, skin moisture, interstitial fluid, intercellular fluid, intracellular fluid, wound exudates, blood, saliva, menstrual fluid, tears, urine, and vaginal fluid that exit the body and enter into the reservoir of the device.

Examples of electrolytes include, but are not limited to, pharmaceutically acceptable organic and organic acids, bases, salts, buffers, peptides, polypeptides, proteins, nucleic acids, and/or other inorganic and organic compounds. Examples of salts include, but are not limited to, chloride salts (such as sodium chloride, potassium chloride, lithium chloride, calcium chloride, strontium chloride, magnesium chloride or other chloride salts), as well as salts of sodium, potassium, lithium, calcium, magnesium, strontium, fluoride, iodide, bromide. Examples of buffers include, but are not limited to, phosphates, citrates, acetates, lactates, and borates.

In one embodiment, the carrier contains a cooling, heating, or fragrance sensate or combination thereof to be used as a sensory cue. In another embodiment, the carrier contains a warming agent, cooling agent, topical analgesic or combination thereof in a therapeutically effective amount to immediately relive pain.

Optionally, menthol is used at a level of about 2 percent to about 40 percent of the carrier, e.g., at a level of about 5 percent to about 30 percent of the carrier. In one embodiment, methyl salicylate is used at a level of about 5 percent to about 60 percent of the carrier, e.g., at a level of about 10 percent to about 40 percent of the carrier. The carrier may be comprised of a skin penetration enhancer such as Quadrol™ or Neutrol™.

Electrodes

In one embodiment of the device configuration, the electrical stimulation is delivered through two separate electrodes in contact with the patient's skin. In another embodiment of the device configuration, two conductive electrodes are in ionic communication with a carrier containing an electrolyte (e.g., ions of one or more electrolytes in the carrier are in contact with the conductive electrode) and the carrier is in ionic communication with the skin. This electrode configuration differs from those in conventional iontophoresis devices in which each conductive electrode is in contact with a separate carrier (e.g., each electrode is contained in a separate compartment and affixed to the skin with electric insulation between them in order that all the electric current travels through the skin to complete the electric circuit). One advantage of this configuration is that the devices can be more versatile in its shape, thus increasing significantly their utility.

The conductive electrode may be made of a metal/metal salt or a metal/nonmetal composite (e.g., held together by polymeric binders). Non-limiting examples of such composite conductive electrodes include (i) electrodes made of powders or flakes of silver, silver chloride, optional conductive carbon, and polymeric binders (e.g., dried coating of conductive silver/silver chloride ink) and (ii) electrodes made of powders or flakes of zinc, optional conductive carbon, and polymeric binders (e.g., dried coating of conductive zinc ink).

The conductive electrodes of the present invention may be reactive conductive electrodes or inert conductive electrodes.

A "reactive conductive electrode" means a conductive electrode that goes through a change in its chemical composition as a result of electrode chemical reactions occurring when electric current passes through the electrode. In one embodiment, the reactive conductive electrode is an anode made of reactive materials such as a pure metal or a metal alloy including, but not limited to, zinc, aluminum, copper, magnesium, manganese, silver, titanium, tin, iron, and alloys thereof. Upon passage of an electric current, metal ions such as zinc, copper, magnesium, manganese and/or aluminum cations are released from the anode into the carrier and delivered into the barrier membrane. Such ions may serve therapeutic benefits such as anti-microbial effects, immunologic modulation, enzymatic regulation, and/or anti-inflammatory effects.

The reactive conductive electrode may be made of reactive materials such as metal halides (e.g., silver-silver chloride (Ag/AgCl), silver-silver bromide, and silver-silver iodide). In this case, the primary electrochemical reaction at the cathode surface is conversion of solid silver halide to metallic silver with little unwanted consumption of the oxidizing agents generated by the anode.

An "inert conductive electrode" means a conductive electrode that does not go through a change in its chemical composition. In one embodiment, the anode is made of an inert conductive electrode.

In one embodiment, the conductive electrode is made of, or coated on the surface of, an inert material such as a noble metal (e.g., gold, platinum, or gold-coated conductive metals), conductive carbon (e.g., glassy carbon or graphite), carbon-embedded polymers (e.g., carbon silicone rubbers), conductive carbon polymer foam or sponge, silver halide-coated silver (e.g., silver chloride-coated silver, silver bromide-coated silver, and silver iodide-coated silver), or corrosive resistant alloys. In another embodiment, a conductive electrode is in the form of a metal sheet, a metal wire, or a metal coated on a metal or nonmetal substrate (e.g., a polymer, natural or synthetic fiber or fabric), or is made by attaching or depositing a conductive electrode material to conductive or nonconductive substrate of a desired size and shape, such as by electroplating, electroless plating, binding with binders (e.g., conductive inks), plasma deposition, spray coating, plasma coating, conductive ink coating, screen printing, dip coating, vacuum deposition, and combinations thereof.

Shape

The device housing can be fabricated into various shapes and sizes to fit the contours of various body parts. For example, the device may be shaped as a flat patch applied to any area of the body, such as the lower back.

In one embodiment, the device conforms to a body part such as a hand, foot, knee, joint, elbow, neck and comprises any shape of a garment such as a belt, glove, sock, mask, knee brace, elbow brace, or shirt. In another embodiment, the device which is designed in the shape of a body part is made up of conductive fibers which deliver the electrical stimulation treatment. In still another embodiment, the conductive fibers may be used to deliver electrical heat.

Activation of Secondary Modality

The secondary modality may be activated in a variety of ways. For example, the electrical stimulation portion of the device may be operated for a programmed period of time, which then shuts off and the refractory period begins. In one embodiment, the secondary modality may be activated at the moment at which the refractory period begins and shuts off when the refractory period ends. In another embodiment, there is a slight delay between when the electrical stimulation portion of the device shuts off and when the secondary modality is activated. That is, the secondary modality delivery means is in an active state during at least a portion of the time the electrical stimulation delivery means is operational.

In one embodiment, the subject has a remote control device which allows the subject to activate the secondary modality when the electrical stimulation portion has entered the refractory period. In another embodiment, there is the ability to switch to the secondary modality on the device. In still another embodiment, a beep, a light or LED, and/or text or image display signals/informs the subject that the refractory period has begun by way of a beep, a light or LED, and/or by a text or image displayed on an information display on the device controller. A portion of the device or remote may also have a display, light or arrow to indicate that the electrical stimulation portion of the device is in a refractory period, or in a "sleep" mode. In still another embodiment, this refractory period may be overridden so that the electrical stimulation portion is reactivated. In still another embodiment, the device indicates to the subject that it is not recommended to override the refractory period.

Method of Use

The present invention also includes a method of reducing pain and/or the symptoms of other inflammatory conditions in a subject experiencing pain and/or other inflammatory conditions. The method includes the step of treating the subject with a device that comprises an electrical stimulation delivery means, and at least one secondary modality delivery means, wherein the secondary modality delivery means is in an active state during at least a portion of a refractory period of the electrical stimulation delivery means.

The pain and/or other inflammatory condition maybe, for example, generalized local pain, chronic pain, joint pain, muscle pain, back pain, rheumatic pain, arthritis, wound treatment, osteoarthritis, and combinations thereof.

Alternatively, the device of the present invention may be utilized to prepare muscles for exertion and or stretching muscles. The device may be used to treat the muscles with an electrical stimulation delivery means, and at least one secondary modality delivery means, wherein the secondary modality delivery means is in an active state during at least a portion of a refractory period of the electrical stimulation delivery means.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

What is claimed is:

1. A therapeutic apparatus comprising:
an electrical stimulation delivery means, and at least one secondary modality delivery means, wherein the secondary modality delivery means is selected from the group consisting of vibration, heat, light, chemical sensate, and combinations thereof, wherein the secondary modality delivery means is in an active state when electrical stimulation is de-activated, wherein the secondary modality means informs a user that the therapeutic apparatus is in a refractory period for electrical stimulation, and wherein the secondary modality delivery means is activated by a user.

2. The apparatus of claim 1, further comprising a controller to switch from the electrical stimulation delivery means to the secondary modality delivery means.

3. The apparatus of claim 1, wherein the secondary modality delivery means provides therapeutic pain relief.

4. The apparatus of claim 1, wherein the secondary modality delivery means is a vibratory modality that has a frequency between about 1Hz and about 30 kHz and an amplitude from about 1 micron to about 3 mm as measured from peak to peak.

5. The apparatus of claim 1, wherein the electrical stimulation delivery means includes an integrated power source and at least two electrodes.

6. The apparatus of claim 1, wherein the secondary modality delivery means is an electrical heating device, an electrical cooling device, or combination thereof 7. The apparatus of claim 5, wherein the power source delivers an electrical stimulation current greater than about 1 milliampere or less than about 1 milliampere.

8. The apparatus of claim 5, wherein the secondary modality delivery means is directionally positioned in-between the at least two electrodes.

9. The apparatus of claim 5, wherein the secondary modality delivery means is adjacently positioned to the at least two electrodes.

10. The apparatus of claim 1, wherein the apparatus is integrated into an article of clothing or footwear.

11. The apparatus of claim 1, wherein the secondary modality delivery means provides a treatment that includes heating and vibration.

12. The apparatus of claim 1, further comprising a controller that controls the electrical stimulation delivery means and the secondary modality delivery means.

13. The apparatus of claim 12, wherein the controller enables a user to operate the apparatus remotely, wirelessly, or a combination thereof.

14. The apparatus of claim 1, wherein the electrical stimulation delivery means operates with a treatment cycle and a refractory cycle, wherein the secondary modality delivery means operates with a treatment cycle and a refractory cycle, and wherein the electrical stimulation refractory cycle overlaps with the secondary modality delivery means treatment cycle.

15. A therapeutic apparatus comprising:
an electrical stimulation delivery means, and at least one secondary modality delivery means, wherein the secondary modality delivery means is selected from the group consisting of vibration, heat, light, chemical sensate, and combinations thereof, wherein the secondary modality delivery means is in an active state when electrical stimulation is de-activated, wherein the secondary modality means informs a user that the therapeutic apparatus is in a refractory period for electrical stimulation, wherein the electrical stimulation delivery means operates with a treatment cycle and a refractory cycle, wherein the secondary modality delivery means operates with a treatment cycle and a refractory cycle, and wherein the electrical stimulation refractory cycle overlaps with the secondary modality delivery means treatment cycle.

16. The apparatus of claim 15, further comprising a controller to switch from the electrical stimulation delivery means to the secondary modality delivery means.

17. The apparatus of claim 15, wherein the secondary modality delivery means provides therapeutic pain relief.

18. The apparatus of claim 15, wherein the secondary modality delivery means is activated without input from a user.

19. The apparatus of claim 15, wherein the secondary modality delivery means is a vibratory modality that has a frequency between about 1 Hz and about 30 kHz and an amplitude from about 1 micron to about 3 mm as measured from peak to peak.

20. The apparatus of claim 15, wherein the electrical stimulation delivery means includes an integrated power source and at least two electrodes.

21. The apparatus of claim 15, wherein the secondary modality delivery means is an electrical heating device, an electrical cooling device, or combination thereof.

22. The apparatus of claim 20, wherein the power source delivers an electrical stimulation current greater than about 1 milliampere or less than about 1 milliampere.

23. The apparatus of claim 20, wherein the secondary modality delivery means is directionally positioned in-between the at least two electrodes.

24. The apparatus of claim 20, wherein the secondary modality delivery means is adjacently positioned to the at least two electrodes.

25. The apparatus of claim 15, wherein the apparatus is integrated into an article of clothing or footwear.

26. The apparatus of claim 15, wherein the secondary modality delivery means provides a treatment that includes heating and vibration.

27. The apparatus of claim 15, further comprising a controller that controls the electrical stimulation delivery means and the secondary modality delivery means.

28. The apparatus of claim 27, wherein the controller enables a user to operate the apparatus remotely, wirelessly, or a combination thereof.

* * * * *